United States Patent [19]

Clarembeau

[11] Patent Number: 6,002,061
[45] Date of Patent: *Dec. 14, 1999

[54] PRODUCTION OF MONOOLEFIN OLIGOMER

[75] Inventor: Michel Clarembeau, Temploux, Belgium

[73] Assignee: BP Amoco Corporation, Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/714,028

[22] Filed: Sep. 11, 1996

[30] Foreign Application Priority Data

Sep. 13, 1995 [EP] European Pat. Off. .............. 95250221

[51] Int. Cl.$^6$ ................................. C07C 2/02; C07C 2/04
[52] U.S. Cl. ............................................ 585/525; 585/510
[58] Field of Search ..................... 585/502, 510, 585/520, 525

[56] References Cited

U.S. PATENT DOCUMENTS

| | | | |
|---|---|---|---|
| 3,997,621 | 12/1976 | Brennan | 260/683.15 B |
| 4,400,565 | 8/1983 | Darden et al. | 585/10 |
| 4,910,355 | 3/1990 | Shubkin et al. | 585/255 |
| 4,956,516 | 9/1990 | Walker et al. | 585/525 |
| 5,068,487 | 11/1991 | Theriot | 585/510 |
| 5,191,140 | 3/1993 | Akatsu et al. | 585/525 |

*Primary Examiner*—Walter D. Griffin
*Assistant Examiner*—Thuan D Dang
*Attorney, Agent, or Firm*—James R. Henes; Stephen L. Hensley

[57] ABSTRACT

A monoolefin oligomerization process which gives high yields of dimer and trimer at high monoolefin conversions in a single stage reaction is described. The process involves contacting a $C_{6-20}$ oligomerizable olefin with a catalyst comprising boron trifluoride and from 0.05 to 2.5 mol %, based on the total quantity of monoolefin being used, of an alcohol catalyst promoter which is added portionwise during the oligomerization. The oligomerization is performed at a temperature of 45–90° C. and under a pressurized atmosphere of boron trifluoride until the monoolefin conversion is at least 90% and the combined total of dimer and trimer in the liquid reaction mixture is at least 70% by weight.

8 Claims, No Drawings

PRODUCTION OF MONOOLEFIN OLIGOMER

BACKGROUND

It is known to produce monoolefin oligomers by use of boron trifluoride as the catalyst together with a co-catalyst component. A variety of co-catalysts have been proposed for this use including water, alcohols, ethers, esters, aldehydes, ketones, and acid anhydrides. Oligomers produced in this manner are useful in the production of synthetic lubricating oils of different viscosities. Typically the production of such products, often referred to as PAOs, involves oligomer fractionation, hydrogenation and back blending to achieve desired properties. Usually the dimers and triers, especially those of 1-decene, are of greatest utility in the production of low viscosity PAOs for various end use applications.

U.S. Pat. No. 4,045,507 to Cupples, et al. describes a multi-stage process for oligomerizing 1-decene which includes use of a series of two or more tank type reactors. The patentees found that the trimer to tetramer ratio decreases with increasing 1-decene conversion in both stages of a two-stage operation, and that this ratio is higher in the second and succeeding reactors. Thus the process described in the patent operates at low conversion in the first stage and at higher conversions in succeeding stages of the process. The patent shows in Examples 5 and 6 of Table I that at 1-decene conversions of 83.4% and 90.5%, the amount of dimer in the product was only 5.2% and 3.8%, respectively. In addition, the combined total of dimer and trier in the products was 47.8% at 83.4% conversion and 38.9% at 90.5% conversion.

To satisfy commercial requirements, it would be highly desirable to provide a single stage process which can be operated at high olefin conversions (e.g., above 90%) and which can produce a reaction mixture containing a combined total of dimer and trimer above 70%, and in which at least 20% (preferably at least 30% and more preferably at least 40%) of the reaction mixture is dimer. This invention makes it possible to achieve all of these goals.

THE INVENTION

In accordance with this invention the oligomerization only requires a single stage reaction using one reactor. In addition, although operated at 1-olefin conversions above 90%, the oligomerization process of this invention gives substantially higher total yields of dimer and trimer than the yields achieved in U.S. Pat. No. 4,045,507 at high conversions. Moreover, by operating in accordance with preferred embodiments of this invention, the amount of dimer present in the reaction mixture can be above 40%. And all of these advantages can be accomplished while at the same time conducting the oligomerization reaction under commercially attractive reaction conditions.

Provided by this invention is a monoolefin oligomerization process which comprises contacting an oligomerizable monoolefin having in the range of 6 to 20 carbon atoms per molecule with a catalyst comprising boron trifluoride and a total in the range of from 0.05 to 2.5 mol %, based on the mols of monoolefin used, of an alcohol catalyst promoter introduced portionwise during the conduct of the oligomerization, at an oligomerization temperature of 45–90° C., and under a pressurized atmosphere of boron trifluoride in the range of 1 to 4 bars gauge until the monoolefin conversion is at least 90% and the combined total of dimer and trimer in the liquid reaction mixture is at least 70%. In this connection, all percentages pertaining to product composition set forth in the specification and claims hereof are in terms of area percentages by gas chromatography conducted using a Hewlett Packard Model HP5890 SerieII gas chromatograph fitted with a Chrompack 60 cm Dexil 300 GC column operated under the following conditions:

Injector temperature: 350° C.

Detector temperature: 350° C.

Oven initial temperature: 70° C.

Oven final temperature: 350° C.

Oven temperature gradient: 10° C./min.

In a preferred embodiment this process is conducted with a linear α-monoolefin having in the range of 8 to 12 carbon atoms per molecule. It is also preferred to conduct the process at an oligomerization temperature of 60–80° C. until (a) the monoolefin conversion is at least 92%, (b) the combined total of dimer and trimer in the liquid reaction mixture is at least 70%, and (c) the liquid reaction mixture contains at least 40% of dimer.

With suitable agitation of the reaction mixture (e.g., mechanical stiring with an input of from 50 to 500 W/m$^3$ and preferably from 75 to 425 W/m$^3$), reaction proceeds at a highly satisfactory rate under the foregoing conditions. Thus reaction periods in the range of two to three hours will often suffice.

Reaction product composition can be monitored by subjecting periodically-taken samples to gas chromatographic analysis. Once the desired product composition has been achieved, the reaction mixture is quenched with water to terminate the oligomerization.

As indicated above, the alcohol catalyst promoter is introduced into the reaction system on a portionwise basis, and at least 20% (preferably at least 40%, more preferably at least 60%, and most preferably at least 80%) of the total amount of the alcohol promoter is introduced into the reactor containing the monoolefin and the pressurized atmosphere of boron trifluoride as the oligomerization reaction proceeds. The balance, if any, of the alcohol promoter is charged to the reactor before commencing the oligomerization reaction. The portionwise feed can be conducted by feeding portions of the total alcohol charge as a series of individual increments over a period of time. In this case the alcohol is caused to enter the system as a discontinuous series of small additions until the preselected amount to be used pursuant to this invention has been introduced into the oligomerization mixture. Alternatively, and preferably, the feed of the alcohol to the oligomerization mixture is conducted slowly and continuously until the total selected amount of the alcohol has been added. In either case the alcohol feed rates should be from 0.8 to 4 parts by weight of alcohol per 1000 parts by weight of olefin per hour, preferably from 1 to 3 parts by weight of alcohol per 1000 parts by weight of olefin per hour, and most preferably from 2 to 2.6 parts by weight of alcohol per 1000 parts by weight of olefin per hour.

Preferably, the amount of alcohol catalyst promoter used is in the range of from 0.1 to 1.5 mol %, based on the mols of oligomerizable monoolefin used in the reaction.

A further important advantage of this invention is the fact that after stripping off the unreacted monomer and recovering the dimer and trimer fractions by distillation, the distillation bottoms represent a highly useful co-product. Upon hydrogenation of these bottoms, products having desirable properties for use as lubricant blending stocks can be produced.

The monoolefins used in the process are preferably vinyl olefins ranging from 1-hexene to 1-eicosene. However oligomerizable $C_6$ to $C_{20}$ internal olefins can also be used in the process. Likewise, mixtures of one or more such internal olefins with one or more vinyl olefins can be used. The vinyl olefin is either a straight chain olefin (no branching) or a remotely-branched olefin such that the terminal double bond is unhindered sterically. Mixtures of such monoolefins can also be used. However, preferably such mixtures are substantially devoid of vinyildene olefins. Preferred linear monoolefins are those having from 8 to 12 carbon atoms. The most preferred monoolefin is 1-decene.

Alcohol promoters that can be used include alkanols having up to about 18 carbon atoms, and preferably up to about 12 carbon atoms, such as, for example, ethanol, 2-propanol, n-butanol, 2-methylpropanol, n-hexanol, n-heptanol, n-octanol, 2-ethylhexanol and n-decanol. More preferably, the alcohol used has up to 6 carbon atoms. The most preferred alcohol is n-butanol. Diols and other polyols can be used, but are less preferred.

Temperatures used in the process are normally in the range of from 45 to 90° C., and preferably from 60 to 80° C.

The boron trifluoride atmosphere within the reactor is typically maintained at a gauge pressure within the range of 1 to 4 bars including 0.05 to 1.5 bars of nitrogen. A preferred pressure range is from 2.5 to 3.5 bars gauge with 1 bar (gauge) of nitrogen.

To terminate the oligomerization reaction when the preselected olefin conversion has been achieved, the reaction mixture is preferably quenched with water or any suitable aqueous solution. Unreacted olefin can be recovered and recycled to an ensuing reaction. For most uses, the recovered oligomer fractions are normally subjected to catalytic hydrogenation under reaction conditions well-known to those skilled in the art.

The following non-limiting examples illustrate the practice and advantages of this invention.

EXAMPLE 1

Oligomerization of 1-decene is conducted using a 2-liter stainless steel pressure reactor equipped with an external electrical heating mantle, a mechanical stirrer, a cooling coil, a thermocouple sensor, a liquid sampling tube, a rupture disk, a nitrogen inlet, a $BF_3$ inlet and a liquid reactant inlet valve. Charged to the reactor are 1200 g of 1-decene and 0.5 g of 1-butanol. The system is purged with nitrogen and then put under a nitrogen blanket (0.1 bar gauge). The temperature of this mixture is maintained at 70° C. by suitably regulating the electrical input of the heating mantle and the flow of cold water through the cooling coil. To this mixture is added 0.05 g of 1-butanol diluted in 1 mL of 1-decene. Then, the system is pressurized at 1.4 bars gauge with boron triluoride. After 30 minutes of stirring at 70° C., 0.4 g of 1-butanol diluted in 1 mL of 1-decene is added to the reaction mixture. After 60 minutes from the pressurization with boron trifluoride—during which time the oligomerization mixture is continuously stirred, and maintained at 70° C. under a boron trifluoride pressure of 1.4 bars (gauge)—the reaction mixture is quenched with 100 mL of water and the temperature of the system is raised to 80° C. and maintained at this temperature for 1 hour. Then the reactor contents are transferred to a separatory funnel to separate the organic and aqueous phases. The organic product mixture is then repeatedly washed with additional separate quantities of water until the water phase used shows no acidity. An organic reaction product formed in this manner was shown by gas chromatography to contain the product distribution (in area percentages which are approximately equal to weight percentages) given in Table 1:

TABLE 1

| Components | Area %, by Gas Chromatography |
| --- | --- |
| Unreacted monomer | 3 |
| Dimer | 49 |
| Trimer | 27 |
| Tetramer | 19 |
| Pentamer | 2 |
| Hexamer | 0 |

EXAMPLE 2

Oligomerization of 19600 kg of 1-decene is conduced under 2.7 bars gauge of $BF_3$ catalyst and using 1.14 mol % of 1-butanol based on the 1-decene charged. The butanol is added at a continuous rate of 60 kg per hour. Reaction temperature is maintained at 70° C. After a total time of 2 hours, the reaction is terminated by quenching the product mixture with water. The typical composition of the reaction mixture formed in this manner is as shown in Table 2.

TABLE 2

| Components | Area %, by Gas Chromatography |
| --- | --- |
| Unreacted monomer | 5 |
| Dimer | 42 |
| Trimer | 37 |
| Tetramer | 12 |
| Pentamer | 4 |
| Hexamer | 0 |

EXAMPLE 3

The reaction product mixture from Example 2 is distilled in a 6-tray Oldershaw column operated under a vacuum of 3–5 mm Hg. After stripping off the unreacted monomer, a dimer-enriched cut boiling in the range of 130–190° C. is collected. This dimer fraction is then hydrogenated using a nickel catalyst supported on alumina. Typical properties of such hydrogenated diner fraction are as shown in Table 3.

TABLE 3

| Property | Measured Value |
| --- | --- |
| Kinematic viscosity at 100° C. | 1.81 cSt (m$^2$/s) |
| Kinematic viscosity at 40° C. | 5.58 cSt (m$^2$/s) |
| Kinematic viscosity at −40° C. | 308 cSt (m$^2$/s) |
| Pour point | −68° C. |
| Flash point | 155° C. |

EXAMPLE 4

The distillation bottoms remaining from the distillation conducted according to Example 3 are subjected to hydrogenation using a nickel catalyst supported on alumina. Table 4 gives typical properties for the resultant hydrogenated heavy oligomer.

TABLE 4

| Property | Measured Value |
| --- | --- |
| Kinematic viscosity at 100° C. | 4.46 cSt (m²/s) |
| Kinematic viscosity at 40° C. | 21.4 cSt (m²/s) |
| Kinematic viscosity at −40° C. | 4445 cSt (m²/s) |
| Viscosity index | 122 |

EXAMPLE 5

The oligomerization procedure of Example 2 is repeated under the same conditions except that the temperature is maintained at 50 ° C. The composition of a typical product mixture formed in this manner is shown in Table 5.

TABLE 5

| Components | Area %, by Gas Chromatography |
| --- | --- |
| Unreacted monomer | 6 |
| Dimer | 26 |
| Trimer | 50 |
| Tetramer | 13 |
| Pentamer | 5 |
| Hexamer | 0 |

EXAMPLE 6

The reaction product mixture from Example 5 is distilled as in Example 3 to yield a dimer fraction having the properties set forth in Table 6.

TABLE 6

| Property | Measured Value |
| --- | --- |
| Kinematic viscosity at 100° C. | 1.70 cSt (m²/s) |
| Kinematic viscosity at 40° C. | 5.10 cSt (m²/s) |
| Kinematic viscosity at −40° C. | 233 cSt (m²/s) |
| Pour point | −75° C. |
| Flash point | 158° C. |

EXAMPLE 7

The distillation bottoms remaining from the distillation conducted as in Example 6 are subjected to hydrogenation using a nickel catalyst supported on alumina. Table 7 gives typical properties of the resultant hydrogenated oligomer.

TABLE 7

| Property | Measured Value |
| --- | --- |
| Kinematic viscosity at 100° C. | 4.50 cSt (m²/s) |
| Kinematic viscosity at 40° C. | 21.6 cSt (m²/s) |
| Kinematic viscosity at −40° C. | 4175 cSt (m²/s) |
| Viscosity index | 124 |

COMPARATIVE EXAMPLE A

When an operation is conducted as described in the example of U.S. Pat. No. 4,950,822 wherein, inter alia, the butanol is used at a concentration of 1.14 mol % the results were as shown in the following table:

| Components | Wt. %, by Gas Chromatography |
| --- | --- |
| Unreacted monomer | 1 |
| Dimer | 2 |
| Trimer | 45 |
| Tetramer | 32 |
| Pentamer | 16 |
| Hexamer | 4 |

What is claimed:

1. A one-stage monoolefin oligomerization process which comprises:

a) contacting in a reactor a linear α-monoolefin having in the range of 6 to 20 carbon atoms per molecule with a catalyst consisting essentially of boron trifluoride and in the range of from 0.1 to 1.5 mol %, based on the total quantity of monoolefin being fed to the reactor, of an alcohol catalyst promoter which is selected from the group consisting of alkanols having up to about 18 carbon atoms and which promoter is introduced continuously into the reactor during the conduct of the oligomerization, at an oligomerization temperature of 60–80° C. and under a pressurized atmosphere of boron trifluoride in the range of 1 to 4 bars gauge, wherein at least 40% by weight of the total amount of alcohol catalyst promoter fed to the reactor during the reaction is introduced into the reactor as the reaction proceeds at a rate equivalent to from 0.8 to 4 parts by weight per 1000 parts by weight of olefin per hour commencing at about the start of the reaction; and b) terminating the reaction after the reaction has proceeded for a period in the range of two to three hours and when the olefin conversion is at least 92% by weight and the combined total of dimer and trimer in the liquid reaction mixture produced is at least 70% by weight, and the liquid reaction mixture produced contains at least 40% by weight of dimer.

2. A process according to claim 1 wherein the linear α-monoolefin has in the range of 8 to 12 carbon atoms per molecule.

3. A process according to claim 2 wherein the linear α-monoolefin is 1-decene.

4. A process according to claim 2 wherein the temperature is maintained at about 70° C. throughout substantially the entire oligomerization.

5. A process according to claim 1 wherein said rate is equivalent to from 1 to 3 parts by weight per 1000 parts of olefins per hour.

6. A process according to claim 1 wherein the alcohol promoter is 1-butanol.

7. A process according to claim 1 wherein the oligomerization reaction is terminated by quenching the reaction mixture with water or an aqueous solution.

8. A process according to claim 1 wherein the liquid reaction mixture is distilled at reduced pressure to (i) strip off unreacted monomer; (ii) recover a dimer- and trimer-enriched distillate fraction, and (iii) provide distillation bottoms; and wherein said distillate fraction and said distillation bottoms are separately hydrogenated.

* * * * *

UNITED STATES PATENT AND TRADEMARK OFFICE
CERTIFICATE OF CORRECTION

PATENT NO.: 6,002,061
DATED: December 14, 1999
INVENTOR(S): Michel Clarembeau

Page 1 of 2

It is certified that error appears in the above-identified patent and that said Letters Patent is hereby corrected as shown below:

Patent reads:

| Col. | Line | | |
|---|---|---|---|
| IN THE ABSTRACT: | | "high yields of diner" | |
| 1 | 2 | should read: "high yields of dimer" | |
| 1 | 14 | "the dimers and triers" | |
| | | should read: "the dimers and trimers" | |
| 1 | 31 | "trier in the products" | |
| | | should read: "trimer in the products" | |
| 3 | 10 | "vinyildene olefins." | |
| | | should read: "vinylidene olefins." | |

UNITED STATES PATENT AND TRADEMARK OFFICE
CERTIFICATE OF CORRECTION

PATENT NO.: 6,002,061
DATED: December 14, 1999
INVENTOR(S): Michel Clarembeau

It is certified that error appears in the above-identified patent and that said Letters Patent is hereby corrected as shown below:

Patent reads:

| Col. | Line | | |
|---|---|---|---|
| 4 | 48 | "hydrogenated diner" should read: "hydrogenated dimer" | |
| 5 | 61 | "1.14 mol % the results" should read: "1.14 mol %, the results" | |

Signed and Sealed this

Fifth Day of September, 2000

Attest:

Attesting Officer

Q. TODD DICKINSON

Director of Patents and Trademarks